(12) United States Patent
Reina et al.

(10) Patent No.: US 9,022,396 B2
(45) Date of Patent: May 5, 2015

(54) PORTABLE X-RAY GRID CABINET

(71) Applicants: Leo Reina, Crystal Lake, IL (US);
James Sorgani, Crystal Lake, IL (US)

(72) Inventors: Leo Reina, Crystal Lake, IL (US);
James Sorgani, Crystal Lake, IL (US)

(73) Assignee: Portable X-Ray Cassette Company, Crystal Lake, IL (US)

( * ) Notice: Subject to any disclaimer, the term of this patent is extended or adjusted under 35 U.S.C. 154(b) by 0 days.

(21) Appl. No.: 13/940,593

(22) Filed: Jul. 12, 2013

(65) Prior Publication Data

US 2013/0300271 A1    Nov. 14, 2013

Related U.S. Application Data

(63) Continuation of application No. 13/463,483, filed on May 3, 2012, now Pat. No. 8,485,537, which is a continuation of application No. 11/900,172, filed on Sep. 10, 2007, now Pat. No. 8,177,242.

(51) Int. Cl.
*B62B 1/00* (2006.01)
*A47B 81/00* (2006.01)
*A61B 6/06* (2006.01)

(52) U.S. Cl.
CPC . *A47B 81/00* (2013.01); *A61B 6/06* (2013.01); *B62B 1/00* (2013.01)

(58) Field of Classification Search
USPC ........ 280/47.131, 47.17, 47.19, 47.24, 47.27, 280/47.28, 47.29; 378/181
See application file for complete search history.

(56) References Cited

U.S. PATENT DOCUMENTS

| | | | |
|---|---|---|---|
| 2,673,626 A | | 5/1950 | Bastin |
| 2,921,694 A | * | 1/1960 | Decker et al. ................. 108/101 |
| 4,300,053 A | * | 11/1981 | Guynes ......................... 378/181 |
| 4,700,373 A | | 10/1987 | Miller |
| 2005/0226391 A1 | * | 10/2005 | Sekol et al. ................... 378/197 |
| 2006/0061053 A1 | | 3/2006 | Cortese |

* cited by examiner

*Primary Examiner* — Katy M Ebner
(74) *Attorney, Agent, or Firm* — Niro, Haller & Niro

(57) ABSTRACT

A radiographic grid cabinet for holding x-ray grids and/or cassettes that can have a vertical structure attached to a flat base with wheels that engage when the device is tilted backward like a handcart so that the cabinet can be easily transported from place to place. Wheels can fold out when needed. The device also can have a support plate that can move vertically on a set of rails or other structure attached to the cart. A thumb controlled pin on a clamp or other locking device can select one of a number of holes in the rails to lock the cabinet into a fixed vertical position. The device can also have a rotating bearing that allows the grid holder to be rotated from a horizontal to a vertical position, or through a vertical position from either of two horizontal positions.

2 Claims, 10 Drawing Sheets

PORTABLE X-RAY GRID CABINET

This is a continuation of application Ser. No. 13/463,483 filed May 3, 2013, now U.S. Pat. No. 8,485,537, issued Jul. 16, 2013 which was a continuation of application Ser. No. 11/900,172 filed Sep. 10, 2007, now U.S. Pat. No. 8,177,242 issued May 15, 2012. application Ser. Nos. 13/463,483 and 11/900,172 are hereby incorporated by reference.

BACKGROUND

1. Field of the Invention

The present invention relates generally to cabinets that contain x-ray grids and more particularly to a portable x-ray grid cabinet that allows raising and lowering of the grid and positioning of the grid horizontally or vertically.

2. Description of the Prior Art

X-ray grids are special filters that improve radiographic images. The grid generally contains metal or fiber filler strips that help prevent ghost and secondary images which produce unwanted noise in the latent image. A quality grid can reduce Moire' patterns, grid aliasing and scanning lines, resulting in a better x-ray image.

Each x-ray cassette using film, or digital cassette using an imaging plate, is inserted behind a grid before use. Films and plates come in different sizes requiring grids of compatible sizes such as 10×12 in., 24×30 cm, 17¼×18⅞ in. and 18×18 in. and larger. Different types of x-ray imaging such as mammography, spinal, chest and others use different grid types. Since grids are typically heavy and fragile, they can be difficult to transport and manipulate. In particular, it can be difficult to hold a grid in place during radiography. A grid cabinet is a structure for holding a grid.

It would be advantageous to have a portable x-ray grid cabinet that could receive grids of different sizes, be moved from place to place by a single person, and hold the grid for exposure during radiography. In order to perform the latter, it would be advantageous if the grid cabinet was adjustable so that the grid could be raised or lowered to any convenient height in either a grid-horizontal or grid-vertical configuration as well as possibly telescoping and/or forming a flat table surface.

SUMMARY OF THE INVENTION

The present invention relates to a radiographic grid cabinet for holding x-ray grids and/or cassettes that can have a vertical structure attached to a flat base with wheels that engage when the device is tilted backward like a handcart so that the cabinet can be easily transported from place to place. In an alternate embodiment, wheels can fold out when needed. The device also can have a support plate that can move vertically on a set of rails or other structure attached to the cart. A thumb controlled pin on a clamp or other locking device can select one of a number of holes in the rails to lock the cabinet into a fixed vertical position. The device can also have a rotating bearing that allows the grid holder to be rotated from a horizontal to a vertical position, or through a vertical position from either of two horizontal positions. The motion can optionally be restricted by the bearing so that the grid holder cannot rotate more than 180 degrees and cannot be turned upside down. This allows slipping in the grid and holding it without retainers. An optional counterweight or counter-balance can be used to make the vertical motion easier. The device can be supplied in different sizes and can be used with different sized grids. The grid assembly can be removable and independently usable for supine x-ray viewing or for other uses.

DESCRIPTION OF THE FIGURES

Certain embodiments of the present invention are shown in the following figures.

Several drawings and illustrations have been presented to aid in understanding the present invention. The scope of the present invention is not limited to what is shown in the figures.

DESCRIPTION OF THE INVENTION

The present invention relates to x-ray grid cabinets and more particularly to a portable x-ray grid cabinet that can be easily moved by one person, can receive a variety of different grids, and can raise or lower the grid to a convenient position horizontally or vertically as well as optionally telescope forward and move to a flat table configuration.

Figure 1:
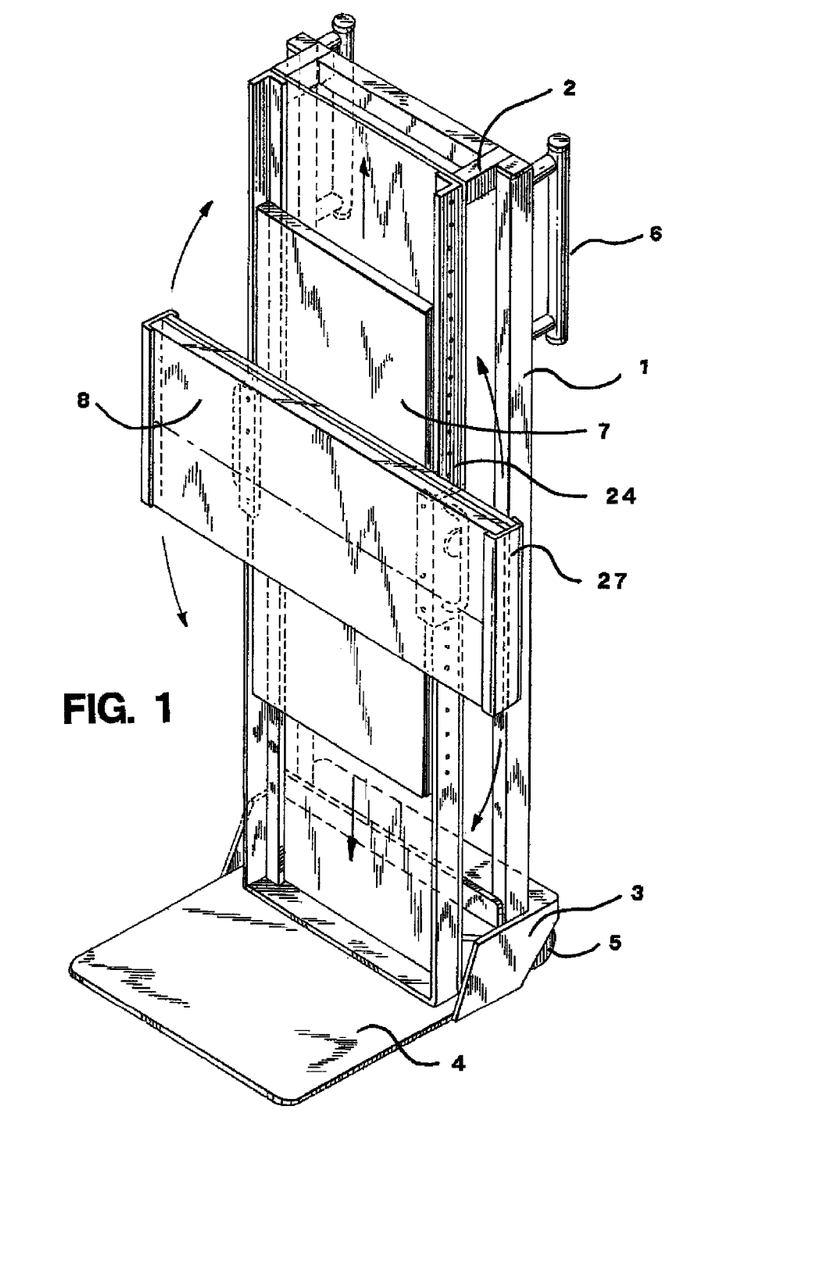
FIG. 1 shows a perspective view of an embodiment of the present invention.
Figure 4:
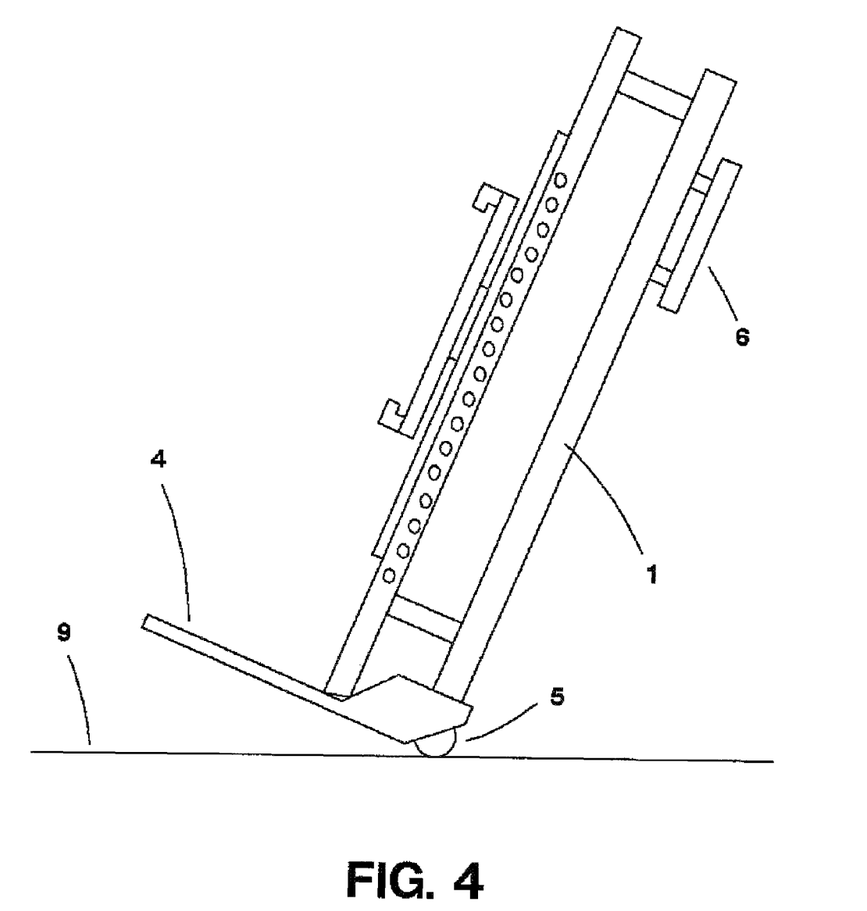
FIG. 4 shows tipping of the device for transport of a grid.

Turning to FIG. 1, a perspective view of an embodiment of the present invention can be seen. This embodiment resembles a hand-cart with a flat plate base member 4, a vertical upright back 1, transportation handles 6 and a set of wheels 5. Because of the particular configuration of this embodiment, the x-ray grid cabinet of the present invention can be easily transported by one person by simply tilting it backward and rolling it on the wheels 5 like a hand-cart. FIG. 4 shows a side view of the device tipped for transport. While a hand-cart type arrangement is desirable, other wheel arrangements are within the scope of the present invention such as folding wheels or any other wheel arrangement.

Returning to FIG. 1, it can be seen in this embodiment that a support plate 7 is mounted on a front set of vertical rails 24 in a manner where the plate can be raised and lowered vertically. This support plate 7 can be locked into a large number of discreet vertical positions. Rotabably attached to the support plate 7 is a grid holder 27 holding a grid 8 (horizontally in FIG. 1). As mentioned, the support plate 7 can move vertically, and hence the slide holder 27 can be rotated horizontally or vertically in a manner that will not allow dropping of the grid 8 from the holder 27 as will be discussed. It is desirable to lock the support plate 7 in one of a number of predetermined vertical positions. This can be accomplished by a thumb activated pin lock. While positive locking with a pin lock is the preferred method, any method of holding the grid at a fixed vertical position is within the scope of the present invention including, but not limited to, pinching, clamping, screwing or any other method of preventing vertical travel.

Figure 2A:
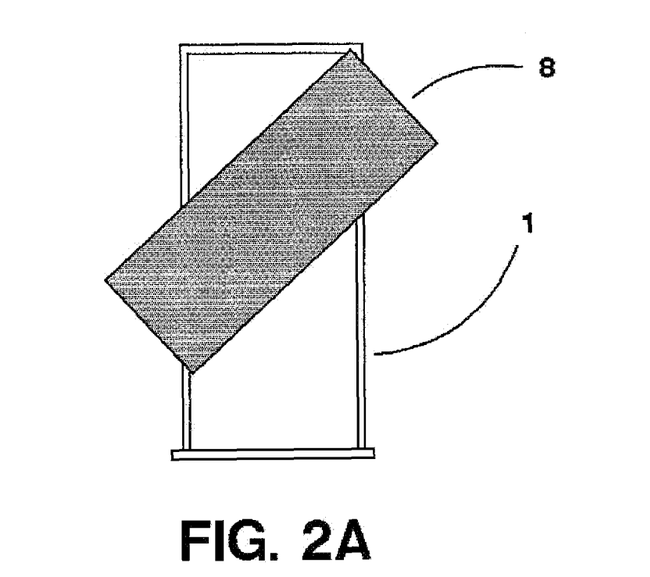
FIGS. 2A-2B are front views of the embodiment of FIG. 1 showing rotation of the grid.
Figure 2B:
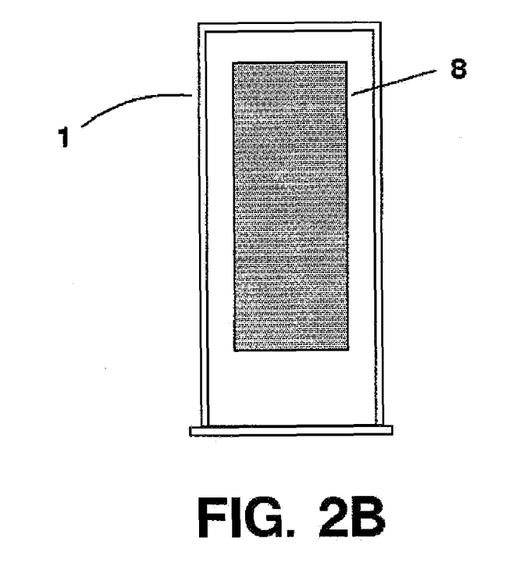

FIGS. 2A-2B show front views of the embodiment of FIG. 1 with the grid holder 8 being in the process of rotation in FIG. 2A and fully rotated to the vertical position in FIG. 2B. The rotation mechanism that will be subsequently discussed can be configured to only allow 180 degrees of rotation in one direction. This allows complete change from a horizontal to vertical configuration, and vice-versa, without being able to turn the grid holder upside down. This in turn allows a convenient slip-in design where the grid 8 is slipped into the grid holder 27 (FIG. 1) and held in by metal fingers and gravity. While it is desirable that the grid 8 slip into and out of the grid holder 27 and remain there without retainers, it is possible to lock the grid in the grid holder using any type of retainer or holding method. Any way of holding the grid in the grid holder is within the scope of the present invention.

Figure 3:
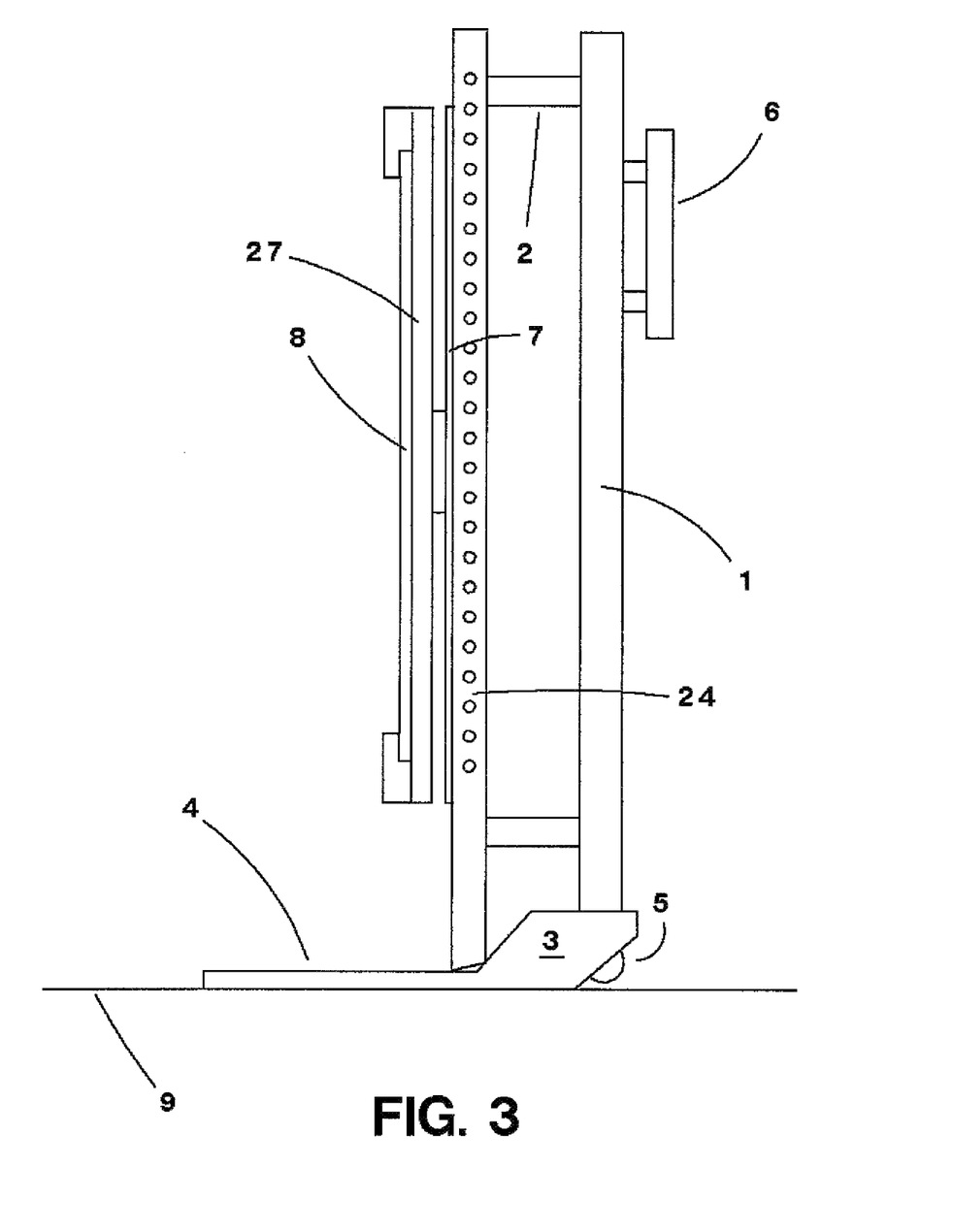
FIG. 3 is a side view of an embodiment of the invention.

FIGS. 3-4 show side views of an embodiment of the invention. The device normally rests on a flat surface or floor 9 and can be supported by its bottom plate 4. A flange 3 on each side contains a set of wheels 5 which engage the floor 9 when the device is tipped as in FIG. 4. A pair of handles 6 allow control and movement of the device. The back frame can be connected with horizontal supports 2 to a pair of vertical front rails 24 that hold the vertical support 7 and hence the grid holder 27 and grid 8. As can be seen from FIG. 4, in the tipped position, the present invention is portable and can easily be used by nurses and technicians to move grids from one location to another. In an alternate embodiment, the grid holder including vertical and rotational movement can be wall-mounted and supplied without the cart.

Figure 5:
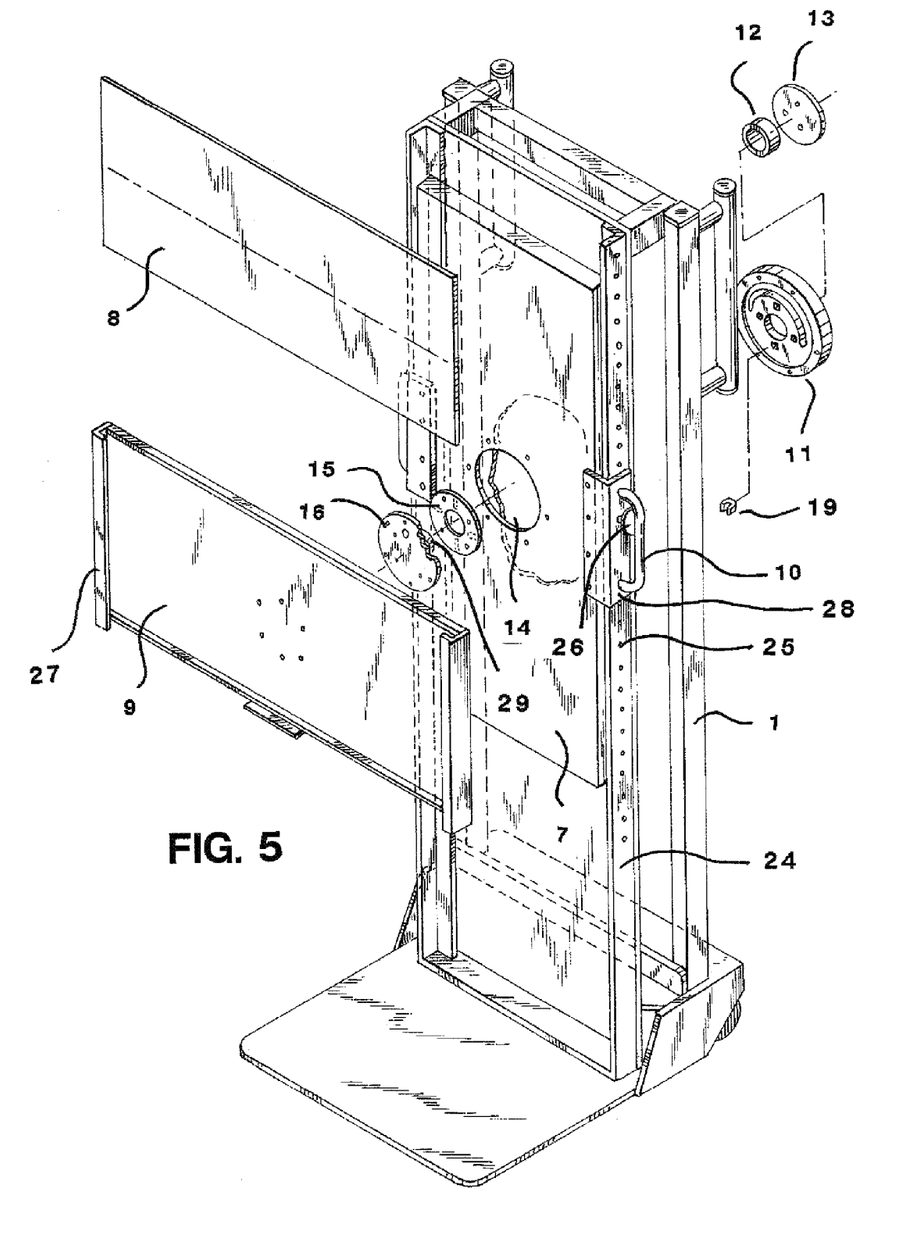
FIG. 5 is an exploded view of the embodiment of FIG. 1.

FIG. 5 shows an exploded view of the embodiment of FIG. 1. It can be seen that the back vertical frame 1 is attached to a set of vertical rails 24 that are set forward of the back frame 1. These rails 24 contain a number of holes 25 that can be engaged by a clamp mechanism 28 and pin 26 that engages one the holes 25. This clamp 28 is attached to the support plate 7 and allows the support plate 7 to be raised or lowered by pulling out on the pin 26 using a thumb latch, changing vertical position, and then allowing the pin 26 to engage a different one of the holes 25. In this manner, the support plate 7 can be adjusted to any convenient vertical position. This process can be aided by one or more oversized handles 10 attached to the clamp 28. The process of vertical movement can also be optionally aided by a counter weight or counterbalance mechanism.

The support plate 7 shown in FIG. 5 has a round hole 14 cut in its interior that receives a bearing body 11 with a slip plate 15 and a bearing front 16. A bearing back 13 mates to a plug or shaft 29 on the slip plate 15 that slides through a bushing 12. The bearing back 13 bolts to the bearing body 11 on the back, and the bearing front 16 bolts to the bearing body 11 from the front through a cabinet plate 9 that is part of the grid cabinet 27. The bearing body 11 thus allows the grid cabinet 9, 27 to rotate 180 degrees in one direction to rest in either a vertical or horizontal position as will be explained.

Figures 6, 7, 8:
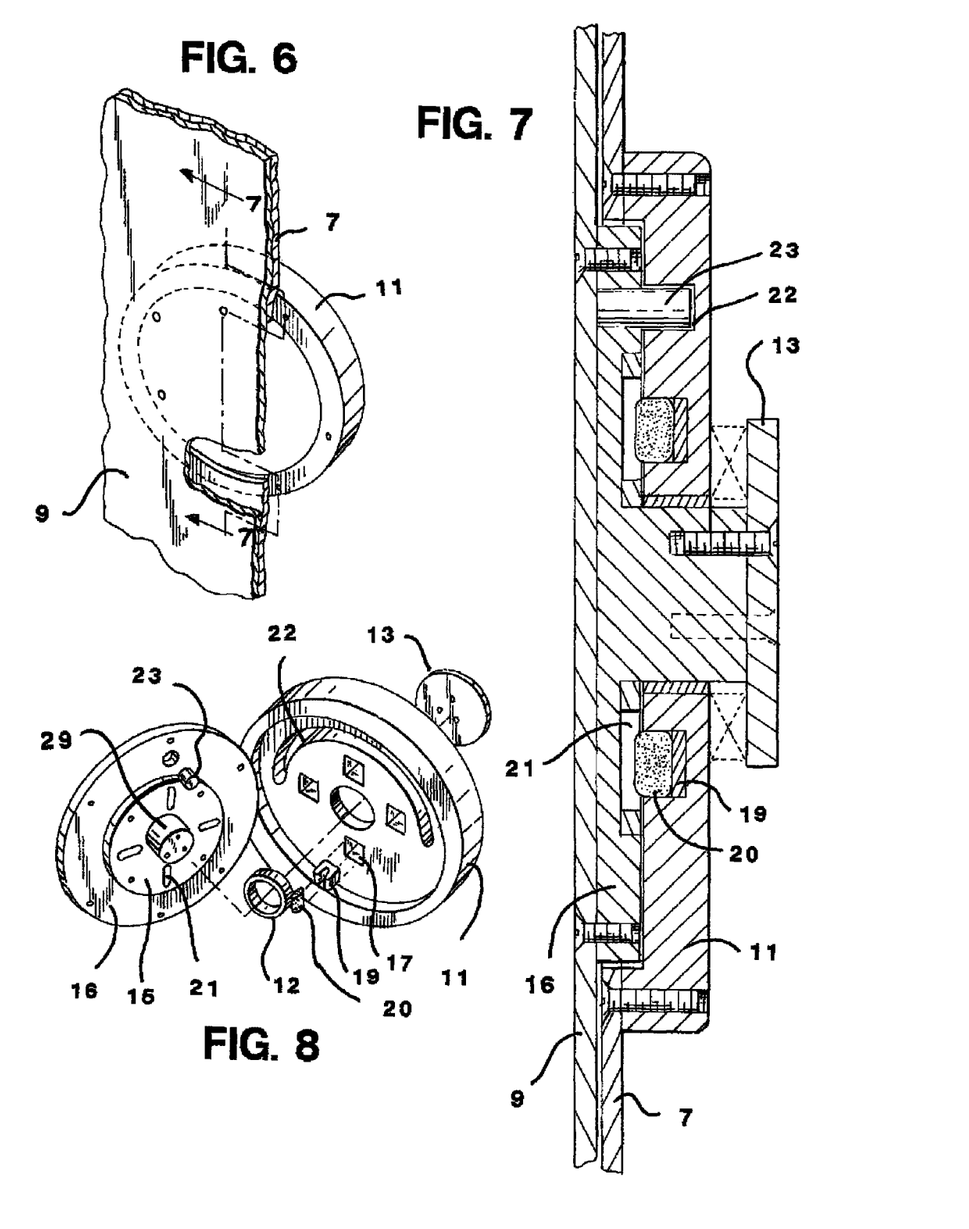
FIG. 6 is a broken out view of an embodiment of the rotation mechanism.
FIG. 7 is a section of FIG. 6.
FIG. 8 is an exploded view of an embodiment of the bearing.

Turning to FIGS. 6-8, the bearing mechanism can be seen in detail. In FIG. 6, the bearing body 11 can be seen passing through the hole 14 in the support plate 7 and mated against the cabinet plate 9. FIG. 7 is a section view of FIG. 6. The bearing back 13 is shown bolted to the bearing front 16. The bearing front 16 is itself bolted to the cabinet plate 9. The bearing front passes through the hole 14 in the support plate 7, and the bearing body 11 is bolted to the support plate 7. In this manner, the cabinet plate 9 rotates in relation to the support plate 7 as the bearing turns.

FIG. 8 shows a broken-apart view of the bearing and can be used with FIGS. 6-7 to understand the functioning of the bearing. The bearing front 16 contains a plug or shaft 29 that passes through a bushing 12 in the bearing body 11 and acts as the main rotation shaft for the bearing. A slip plate 15 is rigidly attached to the bearing front 16 and rotates with it. An optional pin 23 passes out from the bearing front 16 (from a hole) and mates into a groove 22 in the bearing body 11 that makes a 180 degree arc. This groove 22 with the pin 23 engaged only allows 180 degrees of rotation. This allows the cabinet to assume both a horizontal and vertical position but prevents turning it upside down where the grid might fall out. This allows a design where the grid simply slips in and out, but does not need to be retained. While 180 degrees of rotation is the preferred amount of rotation, the present invention can also allow 90 degrees of rotation (or any angle depending on the extent of the groove 22). It is also possible to construct an embodiment of the present invention with total rotation of 360 degrees. In this case, the grid 8 needs to be positively retained in the grid holder 27.

The slip plate 15 has several indents 21 in its inner surface. This slip plate mates with the front-facing surface of the bearing body 11. This front-facing surface of the bearing body 11 has a number of holes 17 that match the indents 21 on the slip plate in four rotational positions. A set of spring holders 19 fit into the holes 17. Each spring holder 19 holds a compressible spring mass 20 which expands into a corresponding indent 21 when aligned. When the bearing is rotated, the spring masses 20 are compressed, and forced out of the indent. When 90 degrees of rotation has occurred, they snap into the next indent 21. This causes the unit to snap into an engaged position at one horizontal position and two vertical positions (the second horizontal position is prevented by the pin 23 and groove 22 mechanism). The grid can thus be rotated by hand from horizontal to vertical and vice-versa with a positive engagement in both vertical and horizontal positions. As stated, it cannot be rotated upside down to where the grid might fall out. While the bearing mechanism shown in FIGS. 6-8 is a preferred embodiment, numerous other bearings and rotation mechanisms are possible. Any rotation mechanism or means is within the scope of the present invention.

The grid cabinet of the present invention can be supplied in various sizes and heights. For example, a 50 inch model can extend and telescope vertically from floor to ceiling. A more typical size is around 34 inches. The device can be adapted to accommodate all types of grids including CR and conventional cassettes known in the art. Any size or type of grid or cassette is within the scope of the present invention. The present invention can be used in the operating room, emergency room, examination room or bedside with the adjustments described providing operation floor to ceiling, vertically and cross-table. Grids can be easily inserted and removed without need for retainers or latching. Vertical adjustment is can be made with the optional oversized handles and quick locking thumb latches (26 in FIG. 5).

Figure 9:
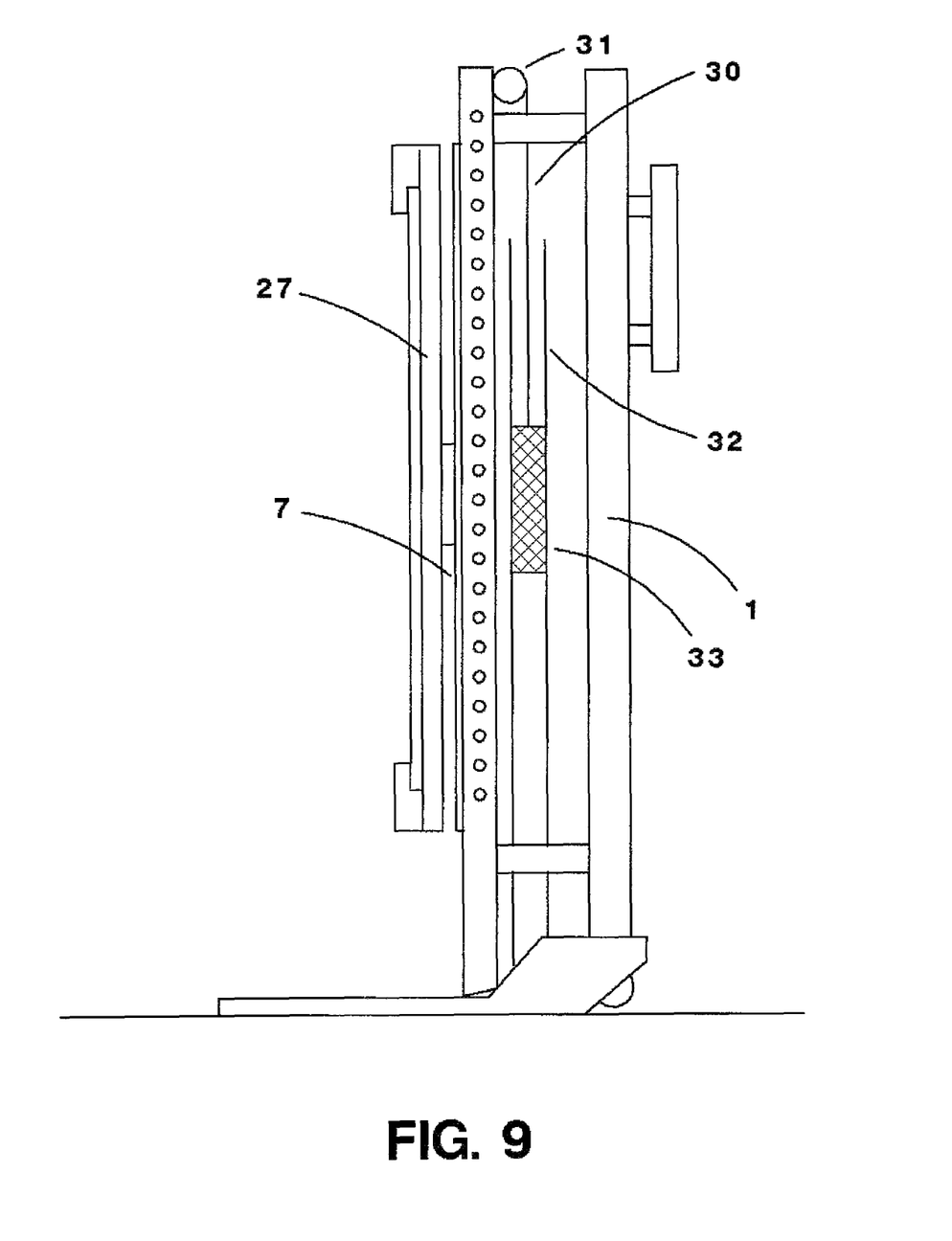
FIG. 9 shows a counterbalance arrangement.

Optionally, the support plate 7 (FIGS. 1, 5) can be attached to a counterbalance weight that allows easier vertical motion. This can be accomplished using a wire line and pulley with a vertically moving weight. FIG. 9 shows a counterbalance arrangement. A wire line 30 is threaded over at least one pulley 31 to a counterbalance weight 33 that descends when the grid ascends and vice-versa. The counterbalance weight 32 moves in a slide 32 that prevents front to back motion when the unit is transported. Any other type of counter weight or counter-balance is within the scope of the present invention.

Figure 10:
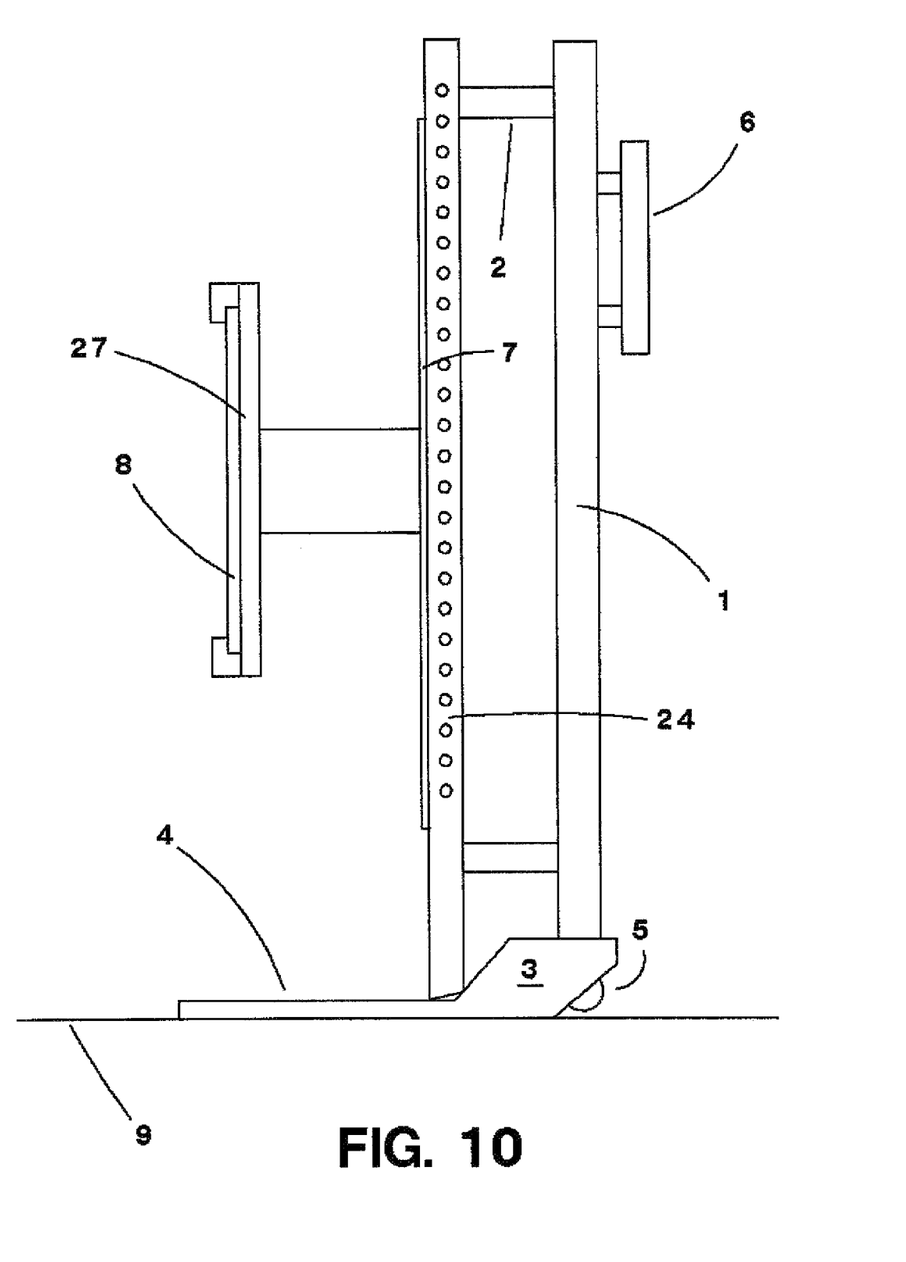
FIG. 10 shows a telescoping embodiment of the present invention.
Figure 11:
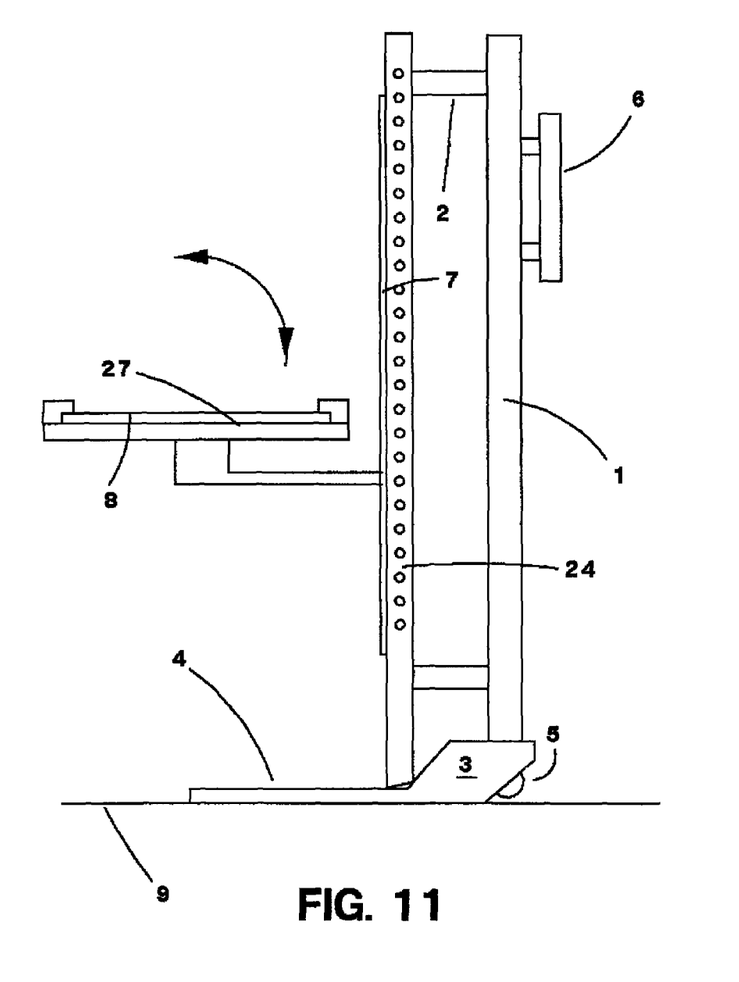
FIG. 11 shows the embodiment of FIG. 10 folded down to a table configuration.

FIG. 10 shows an alternate embodiment of the present invention. Here, the grid 8 and grid holder 27 can be telescoped forward facilitate different types of radiographic exposures. Mechanical telescoping mechanisms are known in the art, and any such telescoping mechanism is within the scope of the present invention. FIG. 11 shows the grid holder 27 rotated from a vertical position to a flat position so that the grid 8 forms a table. The downward and flattening motion can start from a telescoped position. Mechanisms that move from a hanging position to a flat position are known in the art. Any such method of moving the grid from a vertical (hanging) position to a flat table position is within the scope of the present invention.

Figure 12:
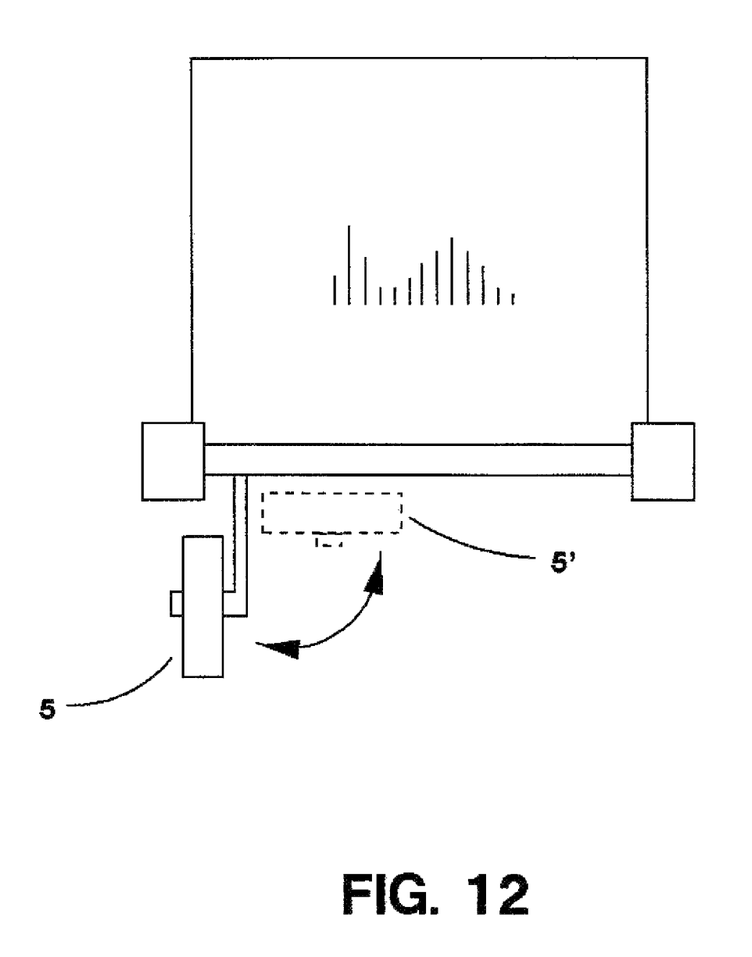
FIG. 12 shows an alternate wheel embodiment with folding wheels.

FIG. 12 shows an alternate method of arranging the wheels 5. In this embodiment, the wheel 5 can have two possible positions: a folded out position 5 and a folded in position 5'. When it is desired to transport the device, the wheels can be moved from the folded in position 5' to the folded out position 5. A second wheel (not shown in FIG. 12) would occupy a symmetric position on the right side of the device also. In normal use, the wheel would not engage the floor 9 until the unit was tipped backward; however, in an alternate design, wheels can be used that continuously engage the floor. In particular, designs with four locked wheels can be used.

Several descriptions and illustrations have been provided to aid in understanding the present invention. One of skill in the art will realize that numerous changes and variations are possible without departing from the spirit of the invention. Each of these changes and variations is within the scope of the present invention.

We claim:

1. A portable radiographic grid cabinet comprising:
a first frame with a base and a pair of uprights, said uprights having top ends and bottom ends, said bottom ends terminating in wheels that engage when said first frame is tilted backward;
a second frame rigidly attached to said first frame, said second frame containing a rotating bearing cooperating with a cabinet plate so that said cabinet plate can continuously rotate between a vertical and a horizontal position, said rotating bearing restricting rotation beyond 180 degrees;
said rotating bearing comprising a bearing body fixed to said second frame and a rotatable slip plate attached to said cabinet plate that mates with said bearing body, said slip plate containing a plurality of indents that can align with a corresponding plurality of compressible spring masses protruding from holes in said bearing body, wherein when aligned, said spring masses enter said indents in the slip plate releasably holding said cabinet plate in a vertical position or one of two horizontal positions;
a grid holder attached to said cabinet plate wherein said cabinet plate holds a radiographic grid;
and wherein said cabinet plate and said bearing can also move vertically up and down along said second frame to a desired vertical position;
a pin in said slip plate or bearing cover attached to said slip plate, said pin aligning with a groove in said bearing body, wherein said pin and groove allow rotation between the first horizontal position, the vertical position and the second horizontal position.

2. The portable radiographic grid cabinet of claim 1 wherein said grid holder can telescope forward and can be moved from a hanging position to a table position.

\* \* \* \* \*